(12) United States Patent
Sun et al.

(10) Patent No.: US 9,265,638 B2
(45) Date of Patent: Feb. 23, 2016

(54) ONE-PIECE STENT IMPLANTER

(71) Applicants: Siyu Sun, Shenyang (CN); Shengjing Hospital of China Medical University, Shenyang (CN)

(72) Inventors: Siyu Sun, Shenyang (CN); Xiaodan Chen, Shenyang (CN); Chuanming Li, Shenyang (CN); Nan Ge, Shenyang (CN); Sheng Wamg, Shenyang (CN); Jintao Guo, Shenyang (CN); Derong Leng, Shenyang (CN)

(73) Assignees: Siyu Sun, Shenyang (CN); SHENGJING HOSPITAL OF CHINA MEDICAL UNIVERSITY, Shenyang (CN)

( * ) Notice: Subject to any disclaimer, the term of this patent is extended or adjusted under 35 U.S.C. 154(b) by 0 days.

(21) Appl. No.: 14/395,489

(22) PCT Filed: Aug. 18, 2013

(86) PCT No.: PCT/CN2013/081712
§ 371 (c)(1),
(2) Date: Oct. 19, 2014

(87) PCT Pub. No.: WO2014/153914
PCT Pub. Date: Oct. 2, 2014

(65) Prior Publication Data
US 2015/0133925 A1 May 14, 2015

(30) Foreign Application Priority Data
Mar. 29, 2013 (CN) .......................... 2013 1 0108643

(51) Int. Cl.
| A61F 2/962 | (2013.01) |
| A61B 18/14 | (2006.01) |
| A61B 17/34 | (2006.01) |
| A61F 2/966 | (2013.01) |
| A61B 18/00 | (2006.01) |
| A61B 17/11 | (2006.01) |
| A61F 2/95 | (2013.01) |

(52) U.S. Cl.
CPC ............. *A61F 2/962* (2013.01); *A61B 17/3468* (2013.01); *A61B 18/14* (2013.01);
(Continued)

(58) Field of Classification Search
CPC ........... A61F 2/95; A61F 2/962; A61F 2/966; A61F 2002/9517; A61F 2/954; A61F 2/958; A61F 2/97; A61F 2/24; A61F 2/2427; A61F 2/01; A61F 2/013; A61F 2/02; A61F 2/04; A61F 2002/011; A61F 2002/016; A61F 2002/018; A61B 18/1477; A61B 18/1487; A61B 2018/00148; A61B 17/3468; A61B 17/3476; A61B 17/3478
See application file for complete search history.

(56) References Cited

U.S. PATENT DOCUMENTS

| 5,482,054 A * | 1/1996 | Slater et al. .................... 600/564 |
| 8,439,934 B2 * | 5/2013 | Satasiya et al. ................ 606/108 |

(Continued)

FOREIGN PATENT DOCUMENTS

| CN | 1342443 A | 4/2002 |
| CN | 1756572 A | 4/2006 |

(Continued)

*Primary Examiner* — Jonathon W Miles
*Assistant Examiner* — Lucas Paez
(74) *Attorney, Agent, or Firm* — CBM Patent Consulting, LLC

(57) ABSTRACT

The invention discloses a one-piece stent implanter, including a front handle and a rear handle; the front end of the front handle is provided with an outer pipe whose top is flexibly connected with a cautery tip, the outer pipe is internally provided with a middle pipe and a stent; the rear handle includes a stainless steel pipe for supporting and an inner pipe positioned in the stainless steel pipe, the top of the inner pipe is fixedly connected to the cautery tip; one end of the middle pipe is mutually touched and connected with one end of the stent, while the other end of the middle pipe is mutually connected with the stainless steel pipe; one end of the stent is close to the cautery tip, with a certain gap kept; when the front handle is retreated along the stainless steel pipe, the outer pipe simultaneously retreats and separates from the cautery tip, positions of the middle pipe and the rear handle remain unchanged, and the stent is automatically released. The invention wherein the stent can be directly implanted into a nidus organ incised and an access from the outside to the nidus organ is established, so that other medical apparatuses and instruments can be continuingly used for removal (including other surgeries) of infectious agents or necrotic tissues, thus increasing comprehensiveness of surgeries and avoiding patients from suffering from repeated operations.

6 Claims, 5 Drawing Sheets

(52) U.S. Cl.
CPC ......... *A61B18/1477* (2013.01); *A61B 18/1487* (2013.01); *A61F 2/966* (2013.01); *A61B 17/3476* (2013.01); *A61B 17/3478* (2013.01); *A61B 2017/1139* (2013.01); *A61B 2018/00148* (2013.01); *A61F 2002/9517* (2013.10)

(56) References Cited

U.S. PATENT DOCUMENTS

| | | | |
|---|---|---|---|
| 8,454,597 B2 * | 6/2013 | Scopton et al. | 606/48 |
| 2003/0018343 A1 | 1/2003 | Mathis | |
| 2003/0074043 A1 * | 4/2003 | Thompson | 623/1.11 |
| 2004/0267281 A1 * | 12/2004 | Harari et al. | 606/108 |
| 2007/0112422 A1 | 5/2007 | Dehdashtian | |

FOREIGN PATENT DOCUMENTS

| | | |
|---|---|---|
| CN | 101347361 A | 1/2009 |
| CN | 201578402 U | 9/2010 |
| CN | 203122694 U | 8/2013 |
| EP | 1985261 A2 | 10/2008 |
| WO | 94/20026 A1 | 9/1994 |
| WO | 2006/069424 A2 | 7/2006 |

\* cited by examiner

ONE-PIECE STENT IMPLANTER

This application is the U.S. national phase of International Application No. PCT/CN2013/081712 Filed on 18 Aug. 2013 which designated the U.S. and claims priority to Chinese Application No. CN201310108643.3 filed on 29 Mar. 2013, the entire contents of each of which are hereby incorporated by reference.

FIELD OF THE INVENTION

The invention relates to a medical device, in particular to an implanter capable of penetrating through lumen wall, specifically to a one-piece stent implanter integrating puncturing stoma with implanting function.

BACKGROUND OF THE INVENTION

Stent implantation is a technology for expansion and recanalization of narrow or occlusive blood vessels or orifices for solving blind area of traditional surgeries by using puncture, catheter dilation, balloon dilation and metallic stent implantation, etc. At present, stent implantation has been widely used applied, and widely accepted in terms of effectiveness. Stent implantation has the advantages of low risk, minimal invasion, less pain, short time of operation, low cost and so on, widely used in benign or malignant obstruction, fistulization and anastomosis.

In case of obstruction of human body's organ channels, physicians often need eliminate obstruction by performing surgical operations or rebuilding physiological channels, and remove necrotic tissues or infectious agents in allowable conditions. This method has the advantages of higher success rate and less postoperative complications. However, at present, frequently used implanters only play a role in conveying a stent to human body's target location. In the process of reconstruction of human body channel (for example, pancreatic pseudocyst, digestive tract cholecyst anastomosis and gastroenterostomy, etc.), prior to stent placement, target organ wall or human body channel is penetrated through by using a puncture needle, an incision knife or laser for reconstruction and channel dilation under ultrasonic guidance of an endoscope, after above-mentioned appliances are retreated out, relevant instruments are placed at the position penetrated for continuous drainage of fluid. Organ shrink may be resulted from rapid drainage of organ contents once appliances for dilation and channel reconstruction are retreated out during above-mentioned surgical operations, which may bring difficulty in follow-up operations and even lead to abdominal contamination. Failure of implanting a drainage device into a gallbladder may result in severe complications (for example, abdominal infection and the like), let alone reach a therapeutic effect.

SUMMARY OF THE INVENTION

Invention objective: the invention aims at solving technical problems in allusion to disadvantages of the prior art by providing a one-piece stent implanter.

For solving the above-mentioned technical problems, the invention discloses a one-piece stent implanter, including a front handle and a rear handle; the front end of the front handle is provided with an outer pipe whose top is flexibly connected with a cautery tip, the outer pipe is internally provided with a middle pipe and a stent; the rear handle includes a stainless steel pipe for supporting and an inner pipe positioned in the stainless steel pipe, the top of the inner pipe is fixedly connected to the cautery tip;

one end of the middle pipe is mutually touched and connected with one end of the stent, while the other end of the middle pipe is mutually connected with the stainless steel pipe; one end of the stent is close to the cautery tip, with a certain gap kept;

When the front handle is retreated along the stainless steel pipe, the outer pipe simultaneously retreats and separates from the cautery tip, positions of the middle pipe and the rear handle remain unchanged, and the stent is automatically released.

In the invention, the rear handle is provided with a conductive socket which is electrically connected with the inner pipe made from metal conductive materials, and the cautery tip is also made from metal conductive materials. Thereby real-time electro-therapy can be applied to incision positions by using the cautery tip.

In the invention, a developing ring is respectively arranged at the position where the middle pipe is touched and connected with the stent and at the position where the cautery tip is touched and connected with the stent. Thereby the position of the stent can be displayed by an imaging device for more accurately positioning.

In the invention, the rear-end of the front handle is provided with a lock nut for locking the stainless steel pipe and the front handle. The lock nut comprises a sealing ring made from elastic material and a plastic part for clamping back and forth, a center channel is used for penetration of the stainless steel pipe, one end of the plastic part is in screw-thread fit to the rear-end of the front handle; in the process of locking of the lock nut, the elastic material in the middle is compressed by the plastic part so that the elastic material deforms and compresses the stainless steel pipe, thus realizing the objective of locking and positioning.

In the invention, the conductive socket is peripherally provided with a cross-over block.

In the invention, the external surface of the cautery tip is provided with a screw thread.

In the invention, the external surface of the inner pipe is provided with an insulating coating or an insulating layer. The insulating coating is directly coated, and the insulating layer is a laminate structure formed by macromolecule material similar to plastics or other insulating materials.

When in use, the lock nut is locked firstly, the power supply is plugged onto the conductive socket so that the cautery tip is energized; after the duct is expanded, the power supply is unplugged and the lock nut is unlocked, the rear handle remains unmoved, the front handle is retreated and the stent is released.

The invention can realize one-step completion of dilation, reconstruction of fistulous tract and stent placement for internal drainage.

Beneficial effects: the invention has beneficial effects as below:

a. The invention adopts a helical metal cautery tip which is conducive to incising nidus organs and convenient for insertion of instruments;

b. The invention adopts a conductive socket to energize the cautery tip, which is convenient for rapid coagulation of tissues in the process of incision of nidus organs, thus playing a role in stypticity;

c. The invention wherein the stent can be directly implanted into a nidus organ incised and an access from the outside to the nidus organ is established, so that other medical apparatuses and instruments can be continuingly used for removal (including other surgeries) of infectious agents or necrotic tissues, thus increasing comprehensiveness of surgeries and avoiding patients from suffering from twice or thrice intraoperative pain.

BRIEF DESCRIPTION OF THE DRAWINGS

Further detailed description of the invention is made in combination with accompanying drawings and embodiments, in this way, above-mentioned and/or other advantages of the invention become more clearly.

DETAILED DESCRIPTION OF THE EMBODIMENTS

Figure 1:
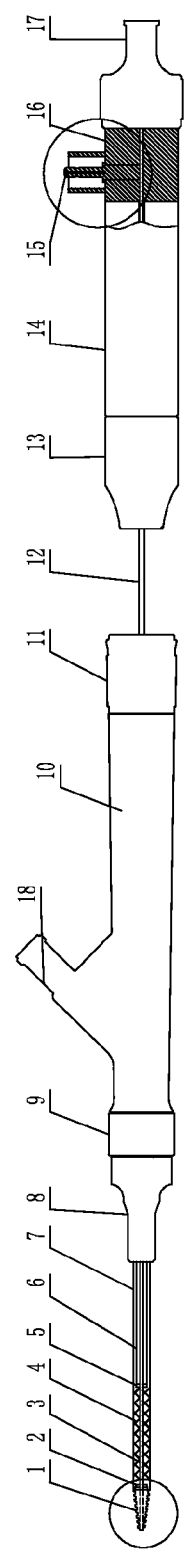
FIG. 1 is a schematic diagram of the external structure of the implanter.

The invention discloses a one-piece stent implanter, including a front handle and a rear handle; the front end of the front handle is provided with an outer pipe whose top is flexibly connected with a cautery tip, the outer pipe is internally provided with a middle pipe and a stent; the rear handle includes a stainless steel pipe for supporting and an inner pipe positioned in the stainless steel pipe, the top of the inner pipe is fixedly connected to the cautery tip; one end of the middle pipe is mutually touched and connected with one end of the stent, while the other end of the middle pipe is mutually connected with the stainless steel pipe; one end of the stent is close to the cautery tip, with a certain gap kept; when the front handle is retreated along the stainless steel pipe, the outer pipe simultaneously retreats and separates from the cautery tip, positions of the middle pipe and the rear handle remain unchanged, and the stent is automatically released. The rear handle is provided with a conductive socket which is electrically connected with the inner pipe made from metal conductive materials, and the cautery tip is also made from metal conductive materials. A developing ring is respectively arranged at the position where the middle pipe is touched and connected with the stent and at the position where the cautery tip is close to the stent. The rear-end of the front handle is provided with a lock nut for locking the stainless steel pipe and the front handle.

In the invention, the conductive socket is peripherally provided with a cross-over block.

In the invention, the external surface of the cautery tip is provided with a screw thread.

In the invention, the external surface of the inner pipe is provided with an insulating coating or an insulating layer.

The invention integrates puncture colostomy and stent placement into a one-piece delivery mechanism. The cautery tip of the implanter is a screw-shaped structure made from metal material, and the rear handle is additionally provided with a conductive socket for energization. Puncturing operation is performed by the implanter via the cautery tip energized, then the stent is released without need for replacing instruments; the cautery tip of the implanter can be cylindrical, conical, cone-shaped or other helical structures; the conductive socket of the implanter is connected and touched well with the inner pipe via a cushion block; the inner pipe of the implanter is a flexible elastic pipe made from biomedical metallic material, the external surface of the inner pipe at the position where the stent is placed is provided with an insulating coating.

EMBODIMENT

The embodiment concretely takes the stent implanter of pancreatic pseudocyst via an endoscope as an example. Under the condition of structure unchanged, the one-piece stent implanter in the invention can be applied to diversified nidus organs, not merely limited to pancreatic pseudocyst.

In the accompanying drawings of the embodiment: 1 cautery tip, 2 far-end developing ring; 3 inner pipe; 4 stent; 5 near-end developing ring; 6 middle pipe; 7 outer pipe; 8 nut; 9 connecting piece; 10 front handle; 11 lock nut; 12 stainless steel pipe; 13 decorative cap; 14 rear handle; 15 conductive socket; 16 cushion block; 17 Luer connector.

Figure 2:
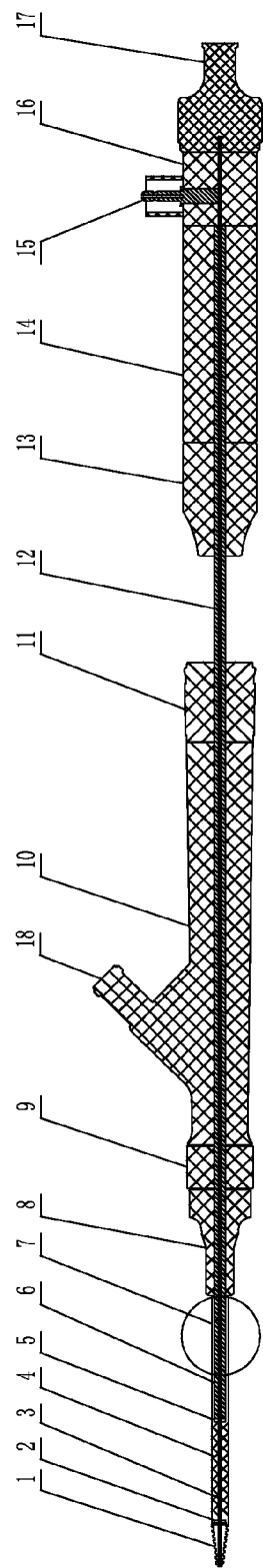
FIG. 2 is a sectional view of the implanter.
Figure 3:
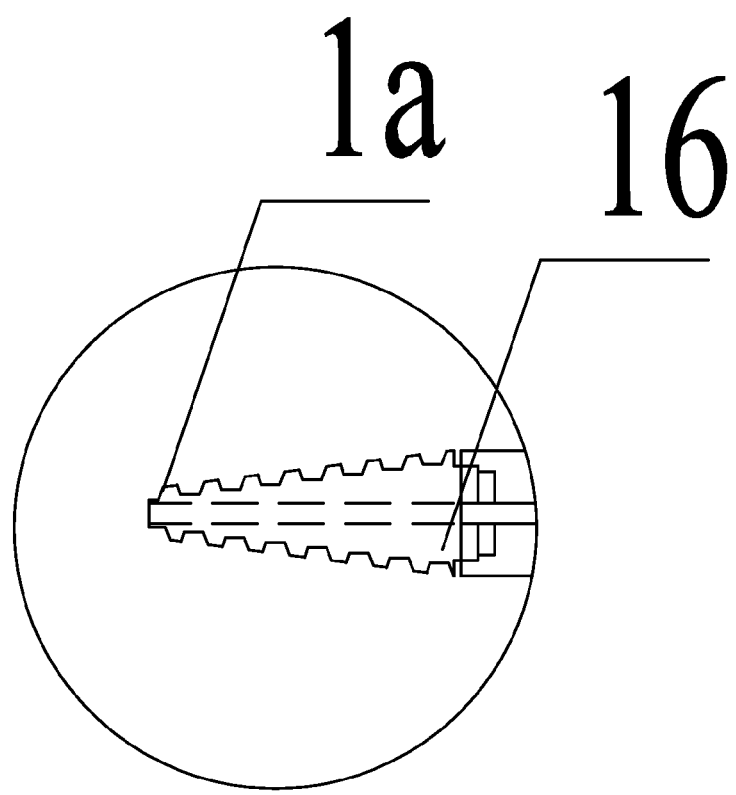
FIG. 3 is a schematic diagram of the cautery tip of the implanter.
Figure 4:
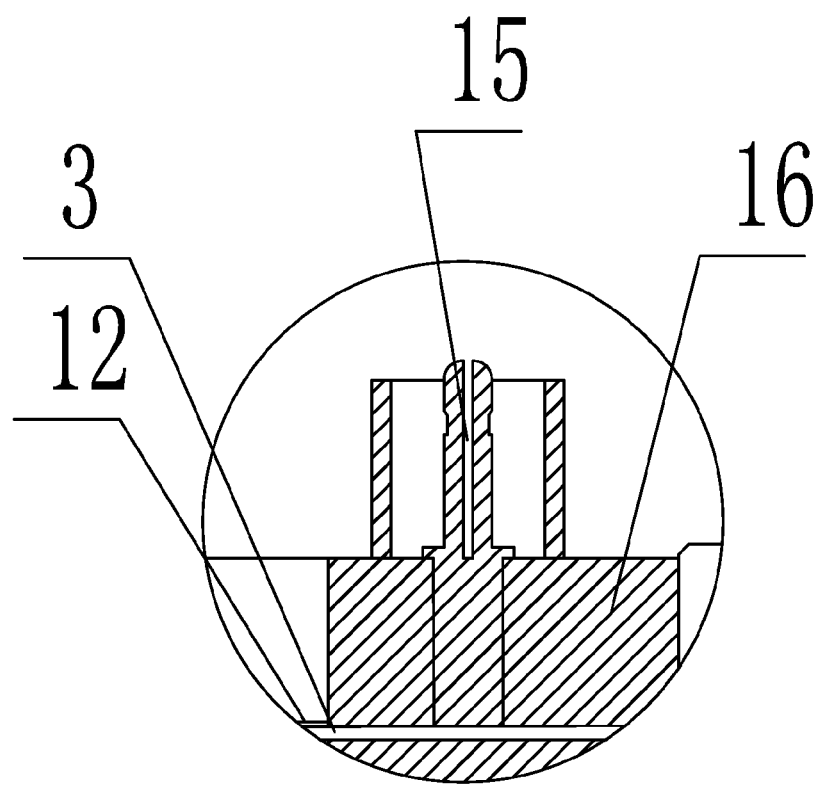
FIG. 4 is a broken-out section view of the rear handle.
Figure 5:
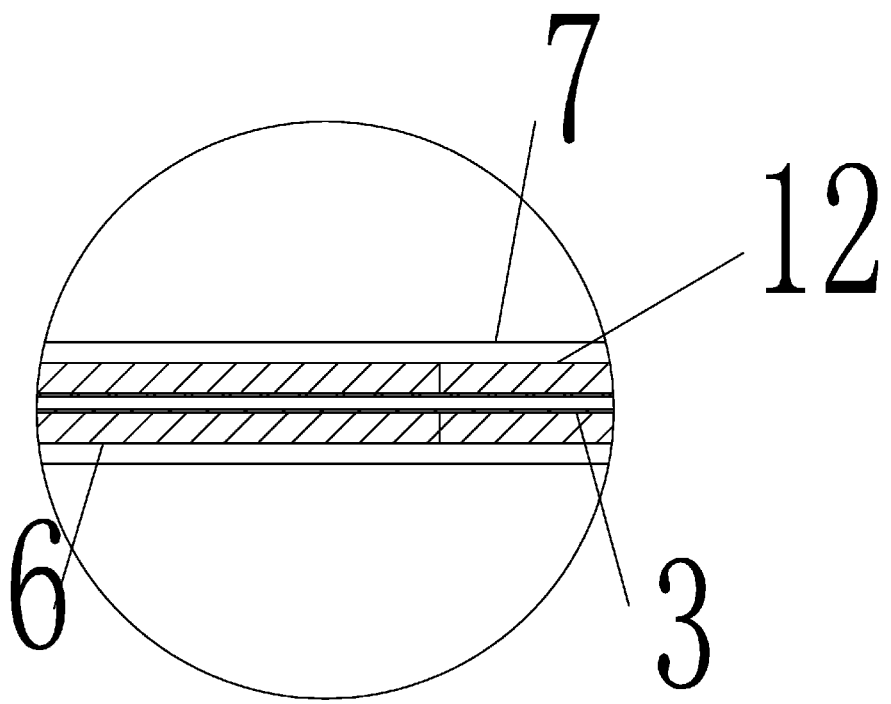
FIG. 5 is a drawing of partial enlargement in FIG. 2.

As shown in FIGS. 1-4, in the embodiment, the middle pipe 6 is sheathed on and articulated with the stainless steel pipe 12, both the stainless steel pipe and the middle pipe 6 are sheathed outside the inner pipe 3, the outer pipe 7 is sheathed outside the stainless steel pipe, the outer pipe is connected with the nut 8, and a connecting piece 9 is arranged at the joint where the nut 8 is connected to the front handle 10. The tail end of the front handle 10 is provided with a lock nut 11, which is used for fixing the front handle 10, the middle pipe 6 and the stainless steel pipe 12. The front end of the front handle 10 is provided with a bypass pipe 18. The far-end of the inner pipe is connected with the cautery tip 1, and the cautery tip 1 is externally provided with a thread structure 1a. When in carrying a stent 4, the far-end of the middle pipe 6 is touched with the stent, the stainless steel pipe passes through the front handle and the rear handle 14, the near-end of the stainless steel pipe is touched with the cushion block 16, the near-end of the inner pipe passes through the cushion block and is pressed by the conductive socket 15 from the upper end. The tail end of the rear handle 14 is provided with a Luer connector 17. Both the far-end developing ring 2 and the near-end developing ring 5 can develop under radiation of X-ray. The nut 8 is connected with the connecting piece 9 and the front handle, playing a role in protection of tube and pipe and convenience for handhold; the decorative cap 13 is connected with the rear handle, playing a role in convenience for handhold.

When in use of the embodiment, different parts are installed successively, the lock nut 11 is locked, the front handle, the stainless steel pipe and the inner pipe are fixed; under guidance of a guide wire and monitoring of X-ray or the endoscope, the implanter is conveyed to the designated lesion location. The conductive socket at the rear handle of the implanter is energized, and the spiral cautery tip energized penetrates through cyst wall. Under the condition of deenergization, the implanter is inserted into the cyst. After reaching the ideal position, the lock nut 11 is unlocked, the front handle 10 retreats, the rear handle 14 remains unchanged in position, at this moment the outer pipe 7 retreats together with the front handle 10, both the inner pipe and the middle pipe 6 remain unchanged in position; at this moment, due to breaking away from sheathing by the outer pipe 7, the elastic stent 4 freely expands and stretches until it is released; after the stent 4 expands and stretches, the inner pipe and the cautery tip withdraws from the space of the stent center, thus achieving the purpose of withdrawing the implanter and guaranteeing unobstructed drainage, also it is available for performing other minimally invasive surgeries such as removal of necrotic tissues if necessary.

The invention provides a one-piece stent implanter. There are many methods and approaches for concrete realization of the technical scheme, and what is mentioned above is only a preferred embodiment of the invention. It shall be pointed out that, those of ordinary skill in the art can, under the premise of not against the inventive principle, make some improvements and embellishment, which shall be regarded within the scope of protection of the invention. Components not explicitly mentioned in the embodiment can be realized by the prior art.

What is claimed is:

1. A one-piece stent implanter, comprising a front handle and a rear handle, wherein a front end of the front handle is provided with an outer pipe, one end of the outer pipe is flexibly connected with a cautery tip, the outer pipe is internally provided with a middle pipe and a stent; the rear handle comprises a stainless steel pipe for supporting an inner pipe positioned in the stainless steel pipe, one end of the inner pipe is fixedly connected to the cautery tip;

one end of the middle pipe is mutually touched and connected with one end of the stent, while the other end of the middle pipe is mutually connected with the stainless steel pipe; one end of the stent is close to the cautery tip, with a certain gap kept;

wherein a rear end of the front handle is provided with a lock nut for locking the stainless steel pipe and the front handle;

when the front handle is retreated along the stainless steel pipe, the outer pipe simultaneously retreats and separates from the cautery tip, positions of the middle pipe and the rear handle remain unchanged, and the stent is automatically released.

2. The one-piece stent implanter of claim 1, wherein the rear handle is provided with a conductive socket which is electrically connected with the inner pipe made from metal conductive materials, and the cautery tip is also made from metal conductive materials.

3. The one-piece stent implanter of claim 2, wherein an conductive socket is peripherally provided with a cross-over block.

4. The one-piece stent implanter of claim 2, wherein an outside of the inner pipe is provided with an insulating coating or an insulating layer.

5. The one-piece stent implanter of claim 1, wherein a developing ring is respectively arranged at the position where the middle pipe is touched and connected with the stent and at the position where the cautery tip is close to the end of the stent, the developing ring can be visualized under radiation of X-ray.

6. The one-piece stent implanter of claim 1, wherein the outside of the cautery tip is provided with a screw thread.

* * * * *